(12) United States Patent
Mueller et al.

(10) Patent No.: US 7,378,658 B2
(45) Date of Patent: May 27, 2008

(54) SECURITY PORTAL WITH THZ TRANS-RECEIVER

(75) Inventors: Eric R. Mueller, West Suffield, CT (US); Raymond Michaud, Lebanon, CT (US)

(73) Assignee: Coherent, Inc., Santa Clara, CA (US)

( * ) Notice: Subject to any disclaimer, the term of this patent is extended or adjusted under 35 U.S.C. 154(b) by 24 days.

(21) Appl. No.: 11/512,693

(22) Filed: Aug. 30, 2006

(65) Prior Publication Data
US 2007/0114418 A1 May 24, 2007

Related U.S. Application Data

(60) Provisional application No. 60/718,650, filed on Sep. 20, 2005.

(51) Int. Cl.
*G01N 21/00* (2006.01)
(52) U.S. Cl. ............... 250/358.1; 250/341.1; 250/330
(58) Field of Classification Search .......... 378/10
See application file for complete search history.

(56) References Cited

U.S. PATENT DOCUMENTS

| | | | |
|---|---|---|---|
| 4,084,158 A | 4/1978 | Slawsby | 342/25 F |
| 4,280,127 A | 7/1981 | Lee et al. | 342/25 A |
| 5,022,091 A | 6/1991 | Carlson | 382/240 |
| 5,936,237 A | 8/1999 | van der Weide | 250/234 |
| 5,969,662 A | 10/1999 | Hellsten | 342/25 A |
| 6,078,047 A | 6/2000 | Mittleman et al. | 250/338.1 |
| 6,150,972 A | 11/2000 | Bickel et al. | 342/25 C |
| 6,525,862 B2 | 2/2003 | Fisher et al. | 359/278 |
| 7,087,902 B2 | 8/2006 | Wang et al. | 250/341.1 |
| 2003/0178584 A1 | 9/2003 | Arnone et al. | 250/495.1 |
| 2004/0061055 A1 | 4/2004 | Kawase et al. | 250/330 |
| 2004/0065831 A1 | 4/2004 | Federici et al. | 250/341.1 |
| 2004/0065832 A1* | 4/2004 | Cluff et al. | 250/341.1 |
| 2004/0140924 A1 | 7/2004 | Keller et al. | 342/22 |
| 2004/0155665 A1 | 8/2004 | Arnone et al. | 324/644 |
| 2004/0252024 A1 | 12/2004 | Huey et al. | 340/540 |
| 2004/0263379 A1 | 12/2004 | Keller | 342/22 |
| 2005/0230604 A1 | 10/2005 | Rowe et al. | 250/221 |
| 2005/0231415 A1 | 10/2005 | Fleischer et al. | 342/22 |
| 2005/0231421 A1 | 10/2005 | Fleisher et al. | 342/179 |

(Continued)

FOREIGN PATENT DOCUMENTS

GB    2 359 716 A    8/2001

OTHER PUBLICATIONS

In re U.S. Appl. No. 11/231,079, filed Sep. 20, 2005, by Eric Mueller, entitled "Identification of Hidden Objects by Terahertz Heterodyne Laser Imaging".

(Continued)

*Primary Examiner*—David P. Porta
*Assistant Examiner*—Yara B Green
(74) *Attorney, Agent, or Firm*—Stallman & Pollock LLP

(57) ABSTRACT

A portal for security screening of transport passengers includes a THz trans-receiver. In one example of the portal, the trans-receiver includes a small-spot, reflective scanning arrangement including a single detector in a heterodyne receiver configuration. In another example, the trans-receiver includes a large-beam reflective scanning arrangement with the trans-receiver in a synthetic aperture radar (SAR) configuration.

19 Claims, 7 Drawing Sheets

U.S. PATENT DOCUMENTS

| | | | |
|---|---|---|---|
| 2005/0232459 | A1 | 10/2005 | Rowe et al. ............... 382/100 |
| 2005/0242287 | A1 | 11/2005 | Hakimi .................. 250/363.09 |
| 2006/0016997 | A1 | 1/2006 | Siegel et al. ........... 250/339.11 |
| 2006/0022140 | A1 | 2/2006 | Connelly et al. ........ 250/338.1 |
| 2006/0055936 | A1 | 3/2006 | Yun et al. .................. 356/479 |
| 2006/0056586 | A1 | 3/2006 | Uetake et al. ................ 378/57 |
| 2006/0104480 | A1 | 5/2006 | Fleisher ..................... 382/103 |
| 2006/0164287 | A1 | 7/2006 | Holt et al. .................... 342/22 |
| 2006/0214107 | A1 | 9/2006 | Mueller .................. 250/341.8 |
| 2006/0235621 | A1 | 10/2006 | Cole et al. .................... 702/19 |
| 2006/0239404 | A1 | 10/2006 | Udpa et al. .................. 378/62 |

OTHER PUBLICATIONS

S. Wang et al., "Tomographic imaging with a terahertz binary lens," *Applied Physics Letters*, vol. 82, No. 12, Mar. 24, 2003, pp. 1821-1823.

J.C. Dickinson et al., "Terahertz imaging of subjects with concealed weapons," *Proceedings of the SPIE*, vol. 6212 (2006), 12 pages in length.

S. Wang et al., "Pulsed terahertz tomography," *Journal of Physics D: Applied Physics*, vol. 37, No. 4, Feb. 21, 2004, pp. R1-R36.

X.-C. Zhang, "Three-dimensional terahertz wave imaging," *Phil. Trans. R. Soc. Lond. A*, vol. 362 (2004), pp. 283-299.

K. L. Nguyen et al., "Three-dimensional imaging with a terahertz quantum cascade laser," *Optics Express*, vol. 14, No. 6, Mar. 20, 2006, pp. 2123-2129.

E.R. Mueller, "Frequency-Shifting Submillimeter Single-Sideband Receiver," *International Journal of Infrared and Millimeter Waves*, vol. 15, No. 4, 1994, pp. 665-670.

F. Huang et al., "Noninvasive Study of Explosive Materials by Time Domain Spectroscopy and FTIR," *AIP Conference Proceedings*, vol. 760, Issue 1, Apr. 9, 2005, pp. 578-585.

D.J. Cook et al., "Quantitative THz Spectroscopy of Explosive Materials," *Optical Society of America (PSI-SR-1196)*, Copyright 2005, 4 pages in length.

F. Oliveira et al., "Analysis of Terahertz Spectral Images of Explosives and Bio-Agents Using Trained Neural Networks," *Proc. SPIE*, vol. 5411 (2004), pp. 1-6.

Powerpoint presentation by J.F. Federici et al., "Terahertz Imaging and Detection of Suicide Bombers," *NJIT Department of Physics*, Funded by US Army and NSF (2005), 16 pages in length.

Article, "Terahertz Scattering for Detection of Improvised Explosive and Bio-agent Dispersal Devices," *Near-Lab (Northwest Electromagnetic and Acoustics Research Laboratory*, printed Sep. 19, 2005, from http://nearlab.ece.pdx.edu/terahertz_imaging.htm web site, 3 pages in length.

* cited by examiner

SECURITY PORTAL WITH THZ TRANS-RECEIVER

PRIORITY CLAIM

This application claims priority to U.S. Provisional Application No. 60/718,650, filed Sep. 20, 2005, the disclosure of which is incorporated herein by reference.

TECHNICAL FIELD OF THE INVENTION

The present invention relates in general to imaging using coherent THz-laser radiation reflected or backscattered from a target by heterodyning the reflected radiation with a signal from another coherent THz radiation source and processing the difference signal to provide an image. The invention relates in particular to an apparatus wherein such an image is used to detect concealed weapons and dangerous substances on or carried by a person.

DISCUSSION OF BACKGROUND ART

The terahertz frequency spectral range is a relatively underdeveloped band of the electromagnetic spectrum. The terahertz band is bordered by the infrared on the short-wavelength side and millimeter-waves on the long-wavelength side. The terahertz band encompasses radiation having a frequency range of 0.3 to 10.0 THz and wavelengths between about 30 micrometers ($\mu$m) and 1 millimeter (mm). The terahertz band is sometimes referred to by practitioners of the art as the far infrared (FIR).

Many materials that are opaque to wavelengths shorter then 30 micrometers are either transparent or semi-transparent in the terahertz band. Such materials include plastic, textiles, paper, cardboard, wood, ceramics, opaque glasses, semiconductors, and the like. Radiation at longer wavelengths, for example, millimeter waves have better transmissivity than terahertz radiation in these materials but the longer wavelengths are unsuitable for use in high resolution imaging systems. Further, such materials do not have much spectral content, i.e., characteristic absorption lines, in these longer wavelength regions that would allow one to be easily distinguished from another.

Terahertz radiation is not an ionizing radiation, so it does not have the potential to present health problems as would, for example, X-radiation (X-Rays). Terahertz radiation can be propagated for much longer distances in the atmosphere than X-rays, for example, several meters, and does not cause damage to electronic devices and unexposed film. In addition to offering a higher potential resolution in imaging than millimeter waves, terahertz radiation also offers a potential to provide sharper differentiation between different materials superimposed on one another and, accordingly provide higher contrast images than would be possible with millimeter waves.

Terahertz radiation has the potential to be useful in security devices for examining persons, luggage or packages for concealed objects or substances. Such objects and substances could include explosives, guns, knives, drugs, biological agents, and the like. Theses objects or substances could be concealed under a person's clothing, or in nonmetallic containers or luggage carried by the person. In order for this potential to be realized there is a need for an adequate terahertz scanning device that can be deployed in airports, train stations, ship ports other transport centers, and public buildings.

SUMMARY OF THE INVENTION

The present invention is directed to apparatus for examining a clothed person for detecting an object or substance concealed by the persons clothing. In one aspect the apparatus comprises a portal defining a position in the apparatus in which the person is positioned for examination. A terahertz (THz) trans-receiver is arranged to provide a beam of THz radiation having a frequency such that the THz radiation is transmitted by the person's clothing.

A optical system is provided for directing a beam of THz radiation from the THz trans-receiver to the positioned person and directing radiation reflected from the positioned person back to the THz trans-receiver. The optical system includes a vertically movable mirror for directing the beam to a plurality of different heights on the positioned person and an angular scanning device for moving the beam to a plurality of different horizontal locations on the person along each of the plurality of different heights. Signal processing electronics are provided for recording data including at least one parameter of radiation reflected from the positioned person at the different heights and locations therealong and for processing the recorded data to provide an image of at least some portion of the positioned person.

In one preferred embodiment of the inventive the apparatus, the movable mirror and the scanning device of the optical system are incorporated in single a scanner head. The scanner head is vertically movable in vertically oriented guides attached to the portal.

In another preferred embodiment of the apparatus, the vertically movable mirror is a ring mirror vertically movable in vertically oriented guides attached to the portal and having a diameter sufficient to encircle the person. The optical system further includes a ring mirror fixedly attached to the portal at a height thereon above the positioned person, and the scanning device is a periscope head including a rotatable mirror. The rotatable mirror directs the THz-radiation beam horizontally to the fixed ring mirror, the fixed ring mirror, directs the THz-radiation beam vertically to the movable ring mirror, and the movable ring mirror directs the THz-radiation beam horizontally to the person.

DETAILED DESCRIPTION OF THE INVENTION

Figure 1:
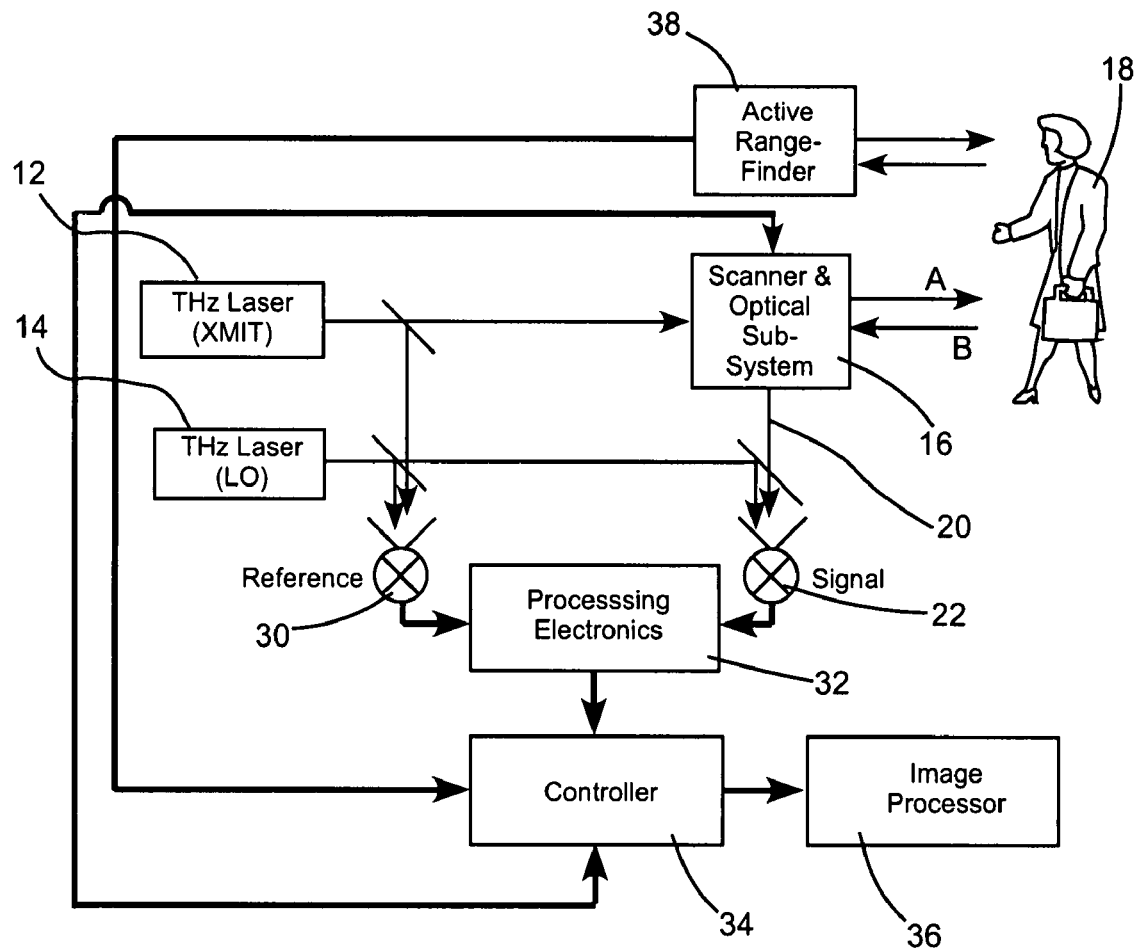
FIG. 1 is a block diagram schematically illustrating functional components of a terahertz heterodyne imaging system in accordance with the present invention including an active range finder, a terahertz trans-receiver, and image processing electronics.

Turning now to the drawings, wherein like features are designated by like reference numerals, FIG. 1 schematically illustrates, in block diagram form a THz imaging arrangement 10 in accordance with the present invention for detecting a concealed weapon, substance, or the like concealed by a person's clothing. Apparatus 10 comprises a THz trans-receiver including one THz-radiation generator 12 functioning as a THz-transmitter, and another THz-radiation generator 14 functioning as a local oscillator (LO). Radiation from the THz transmitter is directed by a scanner and optical sub-system 16 in a direction indicated by arrow A to focus on a target person 18. Reflected radiation from the target person returns to the optical sub-system as indicated by arrow B.

This reflected radiation 20 is directed by the optical subsystem to a THz detector 22. A portion of the THz radiation emitted by THz generator 14 is mixed with the reflected (signal) radiation from the target person to provide a heterodyne signal that is passed to processing electronics 32. Another portion of the THz radiation emitted by THz generator 14 and a portion of the THz radiation emitted by THz generator 12 are directed to a THz detector 30. Here, the two portions are mixed to provide a reference heterodyne signal that is also passed to processing electronics 32. The target and reference heterodyne signals are processed by the processing electronics to provide a signal representative of the strength of THz-radiation reflected from the target person. Operating the scanner provides a plurality of such signals that are passed to a controller 34. Controller 34 provides data on scanner positions corresponding to the signal. The scanner-position data and the signals from processing electronics 32 are processed by an image processor 36 to form an image of the target person.

Imaging system 10 preferably includes an active rangefinder 38 cooperative with controller 34. Rangefinder 38 determines the range from the trans-receiver to the target person. Controller 34 uses the range information cooperative with an active focus control arrangement (not shown) in the trans-receiver to ensure that the THz radiation is always optimally focused on the target person. Preferred range-finding arrangements include a co-aligned optical rangefinder and an ultrasonic rangefinder.

The brief description of the THz imaging arrangement presented above is provided merely to put into perspective mechanical and optical scanning features of the present invention discussed hereinbelow. Several techniques for processing THz-radiation signals are known to those skilled in the art and are applicable to certain embodiments of the present invention. By way of example, a detailed description of processing THz-heterodyne signals is provided in U.S. patent application Ser. No. 11/231,079, filed Sep. 20, 2005, the complete disclosure of which is hereby incorporated herein by reference.

Figure 2:
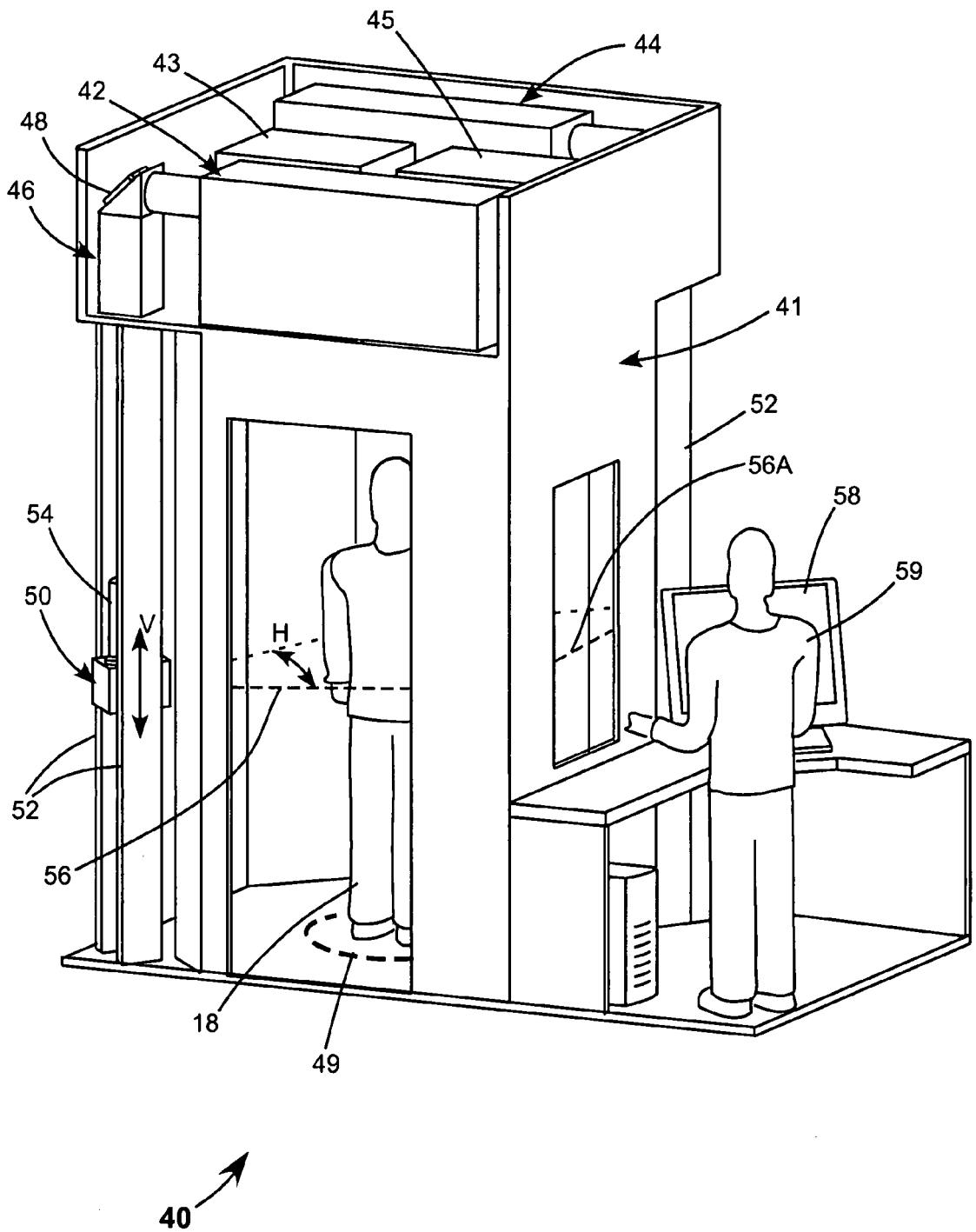
FIG. 2 is a three-dimensional view schematically illustrating one preferred embodiment of a terahertz scanning security portal in accordance with the present invention including two trans-receivers similar to the trans-receiver of FIG. 1 and arranged to scan a person with a small terahertz radiation beam to form an image of the person from a matrix of recorded terahertz reflection data at various beam heights and scan angles, the security portal having two scanning heads each thereof for scanning the beam through a range of angles with the scanning heads arranged to travel vertically up or down, for scanning at different heights.

FIG. 2 schematically illustrates one preferred embodiment 40 of a THz imaging scanner in accordance with the present invention. Scanner 40 is incorporated in a security portal 41. A target person 18 to be examined is required to enter and remain stationary in the security portal. Preferably an area 49 is designated in the portal where the person is optimally positioned for examination. Scanner 40 includes THz trans-receivers 42 and 44. Power supplies and processing electronics for the trans-receivers are located in housings 43 and 45. The manner in which radiation from the THz trans-receivers is delivered to and received from target person 18 is described below with reference only to trans-receiver 42, but is essentially the same for trans-receiver 44.

A beam steering unit 46 including a 45° turning-mirror 48 directs THz radiation from trans-receiver 42 vertically downward as a collimated beam to be received by a scanner head 50. Scanner head 50 is arranged to travel vertically up and down between two guides 52 as indicated by double arrow V. Scanner head 50 includes a variable focus telescope 54 that focuses the collimated beam to a beam 56 on the target person the beam having a small diameter relative to the size of the target person. The diameter of the beam on the target person determines the resolution of the scanner and is preferably about 1 mm in diameter or less. The scanner head also includes a mirror (not shown) that directs beam 56 about horizontally, and scanning optics, for example a galvanometer scanner, within the scanner head cause the beam to swept through an angle across the target person as indicated by double arrow H. The horizontal directing and scanning of the beam may be accomplished by a single mirror. The focus is varied in accordance with rangefinder data to compensate for the changing distance (due to the non-flat shape of the person) of the portion of the person on which the beam is incident. THz radiation reflected from the target person returns to trans-receiver 42 along the delivery path. Recordings of reflected signals at a plurality (N) of different scan angles H (and corresponding different locations on the person) are made at each one of a plurality (M) of different heights V to provide an N×M matrix of signals. This matrix of signals is processed to form an image of at least a selected portion of the target person. The image is presented on a display 58 that can be evaluated by an operator 59 of scanner 40.

Trans-receiver 44 provides another scanned beam 56A incident on the target person on an opposite side of the target person from the side thereof on which beam 56 is incident. There are a number of possible uses for this other scanned beam. One possible use would simply be to provide a more rapid scan of all of the target person than could be provided by a single beam, delivered in this manner, from a single trans-receiver. Here, it is assumed that both beams would have the same frequency.

Another possible use enabled by providing the beams 56 and 56A at different frequencies would be targeting different kinds of concealed materials with the different beam frequencies selected to be optimum for the different materials. This would, require, however, that the target person turn, or be turned, to face each beam in turn.

Those skilled in the art will recognize that while the scanning arrangement of scanner 40 requires only a relatively simple optical system, the arrangement has certain disadvantages. One disadvantage is that each scanned beam is incident on the target person at different incidence angles as the beam is angularly scanned. The beam intensity will be different at different angles of incidence, and the effective thickness of material penetrated by the beams will be different at different incidence angles. This can adversely affect the quality of a displayed image even if some compensation for incidence angle dependence is incorporated in image processing software. If a 360° (all-around) image is required, it is likely that either the target person would be required to turn or be turned, or that additional beams be provided, for example, four beams angularly spaced at 90° to each other.

Providing more beams from correspondingly more THz trans-receivers would increase the cost of the scanning arrangement. Requiring a person to turn in different directions increases the inconvenience of being subjected to scanning. Turning a person on a turntable or the like could be disorienting for a person and may cause anxiety in elderly persons, children, or persons with infirmities.

Figure 3:
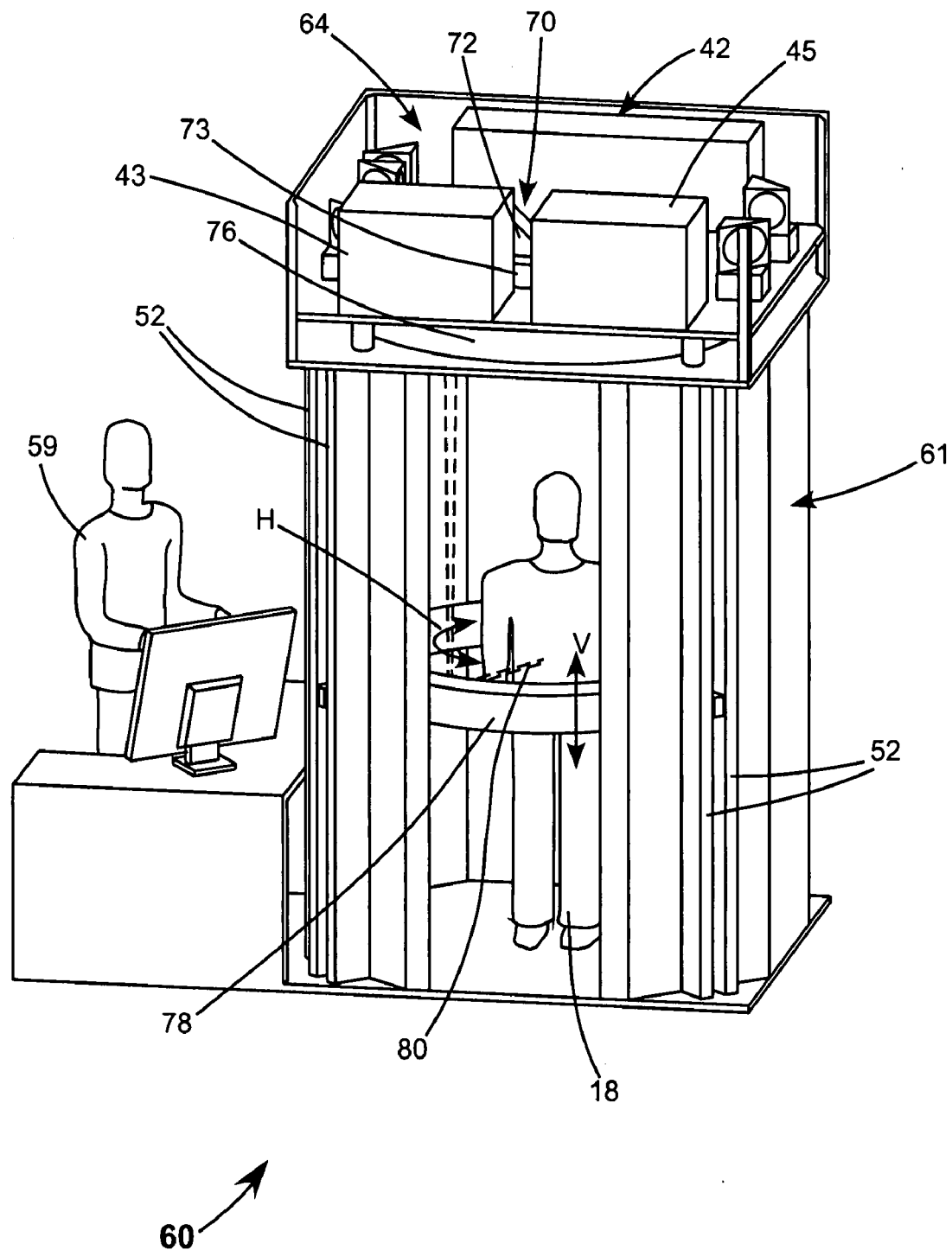
FIG. 3 is a three-dimensional view from the rear schematically illustrating another preferred embodiment of a terahertz scanning security portal in accordance with the present invention including only one trans-receiver similar to the trans-receiver of FIG. 1 and arranged to scan a person with a small terahertz radiation beam to form an image of the person from a matrix of recorded terahertz reflection data at various beam heights and scan angles, the security portal having a single 360°-rotatable periscope head (only a fixed portion thereof shown) cooperative with a fixed ring mirror and a vertical traveling ring mirror arranged such that the small beam can be scanned completely around the person at different heights.
Figure 4:
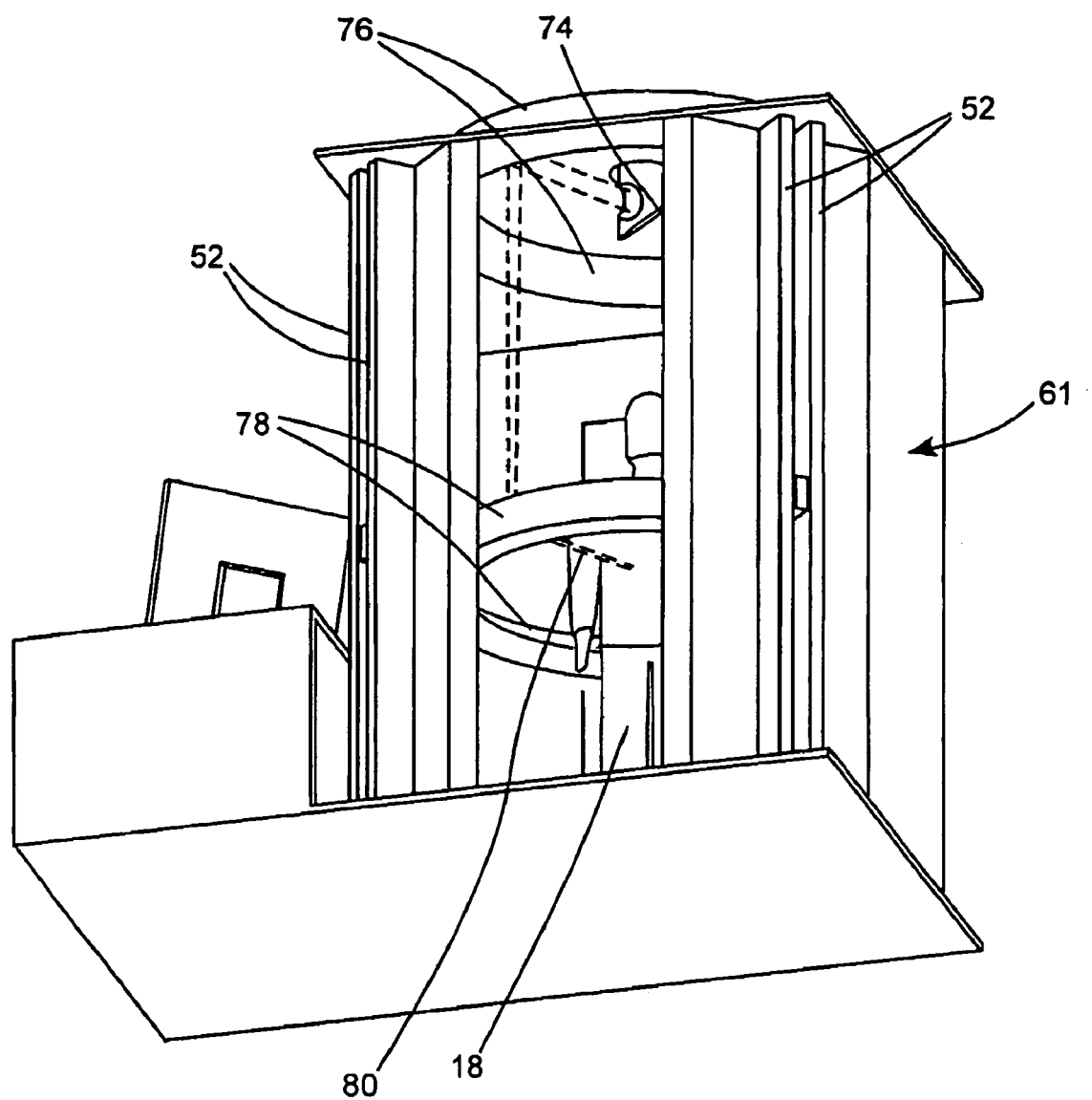
FIG. 4 is a three-dimensional view from below schematically illustrating detail of the rotatable portion of the periscope head and the fixed and traveling ring mirrors of FIG. 3.
Figure 5:
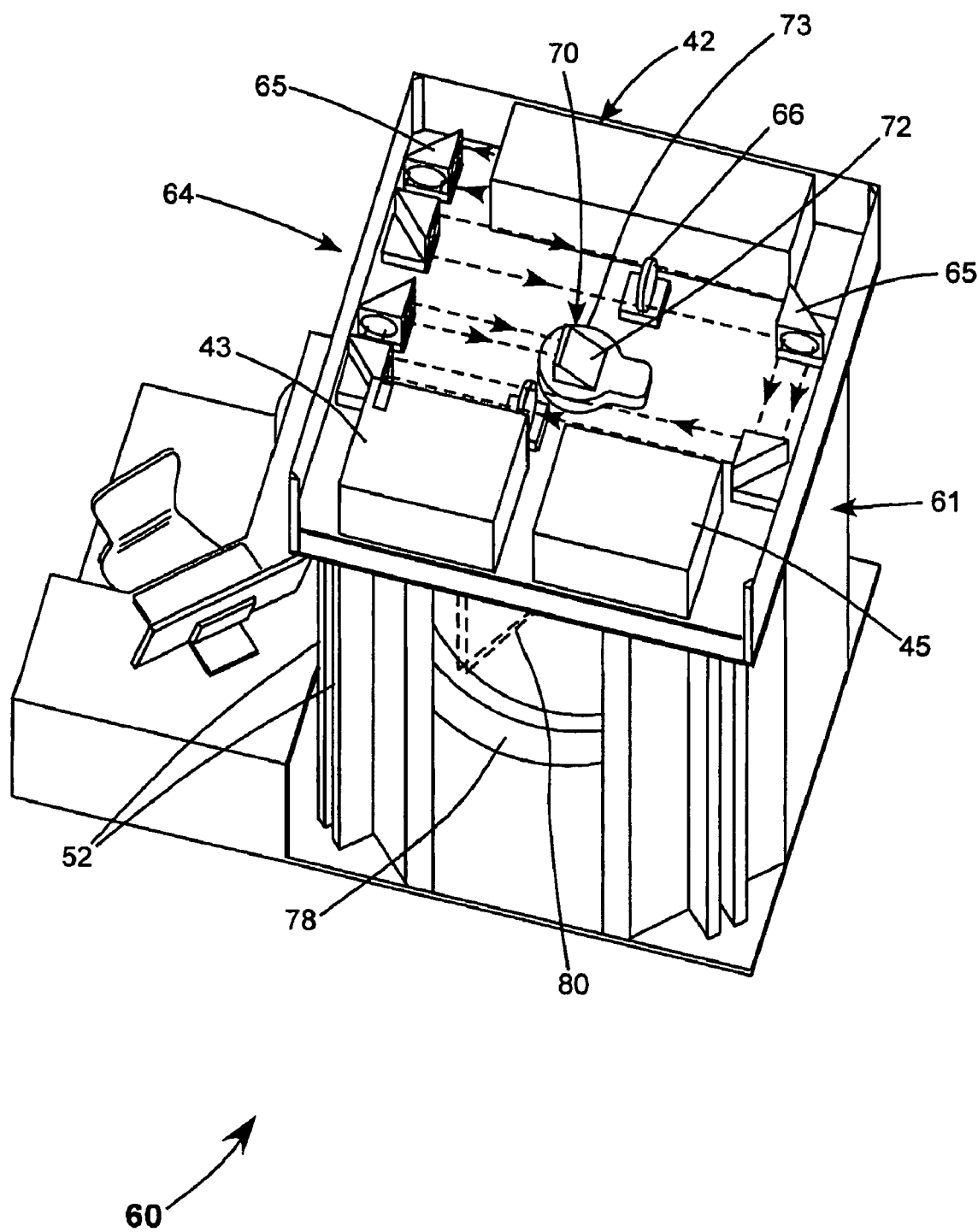
FIG. 5 is a three-dimensional view from above schematically illustrating detail of a beam delivery system delivering terahertz radiation from a terahertz laser of the trans-receiver to the periscope head of FIG. 4 via the fixed portion thereof.

FIG. 3, FIG. 4, and FIG. 5 schematically illustrate another embodiment 60 of a THz imaging scanner in accordance with the present invention. Scanner 60 is designed to avoid the above-discussed disadvantages of above-described scanner 40. Scanner 60 is incorporated in a security portal 61. A target person 18 is required to enter and remain stationary in the security portal within a designated area as discussed above with reference to scanning arrangement 40. Scanner 60 includes only one THz trans-receiver, here, identified as trans-receiver 42.

Beam shaping and steering optics 64 include a plurality of 45° turning-mirrors 65 and lenses 66. Radiation from THz trans-receiver 42 (the radiation being designated by long-dashed bounding lines with arrows indicating propagation direction in FIG. 3) is directed by optics 64 into a periscope head 70. Periscope head 70 includes a fixed 45° turning-mirror 72 that directs the THz radiation vertically downward to a rotatable 45° turning-mirror 74. This rotatable mirror is driven by a motor 73 and is capable of rotation through 360°. Rotatable 45° turning-mirror 74 directs the THz radiation horizontally outward to a fixed ring-mirror 76. Ring-mirror 76 directs the radiation vertically downward to a ring-mirror 78 that is movable vertically in pairs of guides 52 (here, 4 pairs) as indicated by double arrow V. Ring-mirror 78 has a diameter the same as that of fixed ring-mirror 76 and wide enough to comfortably encircle target person 18.

Optics 64 and ring-mirrors 76 and 78 are configured such that the THz radiation is directed horizontally to the target person and focused in a beam 80 having a maximum transverse dimension corresponding to the desired resolution of the scanner, preferably about 1 mm or less as discussed above with reference to scanner 40 of FIG. 2. The term "maximum transverse dimension" here recognizes that transverse cross-section of the beam may not be exactly round in a cylindrical configuration of the ring mirrors. The focusing optics are preferably variable focus optics as discussed above.

Rotating turning-mirror 74 of periscope 70 through 360° causes beam to 80 to travel around ring-mirror 78, as indicated in FIG. 3 by double arrow H, while continually pointing toward the target person. THz radiation reflected from the target person returns to trans-receiver 42 along the delivery path. Recordings of reflected signals at a plurality (N) of different radial directions H are made at each one of a plurality (M) of different heights V to provide an N×M matrix of signals that can be processed to form an image of all or some portion of the target person as discussed above.

An advantage of scanner 60 is that the target person can remain stationary throughout the scanning process. Further, the scanning beam is a generally at normal incidence throughout the whole range of scan angles. The terminology "generally at normal incidence" here acknowledges that there may be some variations from normal incidence due to local slope variations at different points of incidence of beam 80 on the target person.

Figure 6:
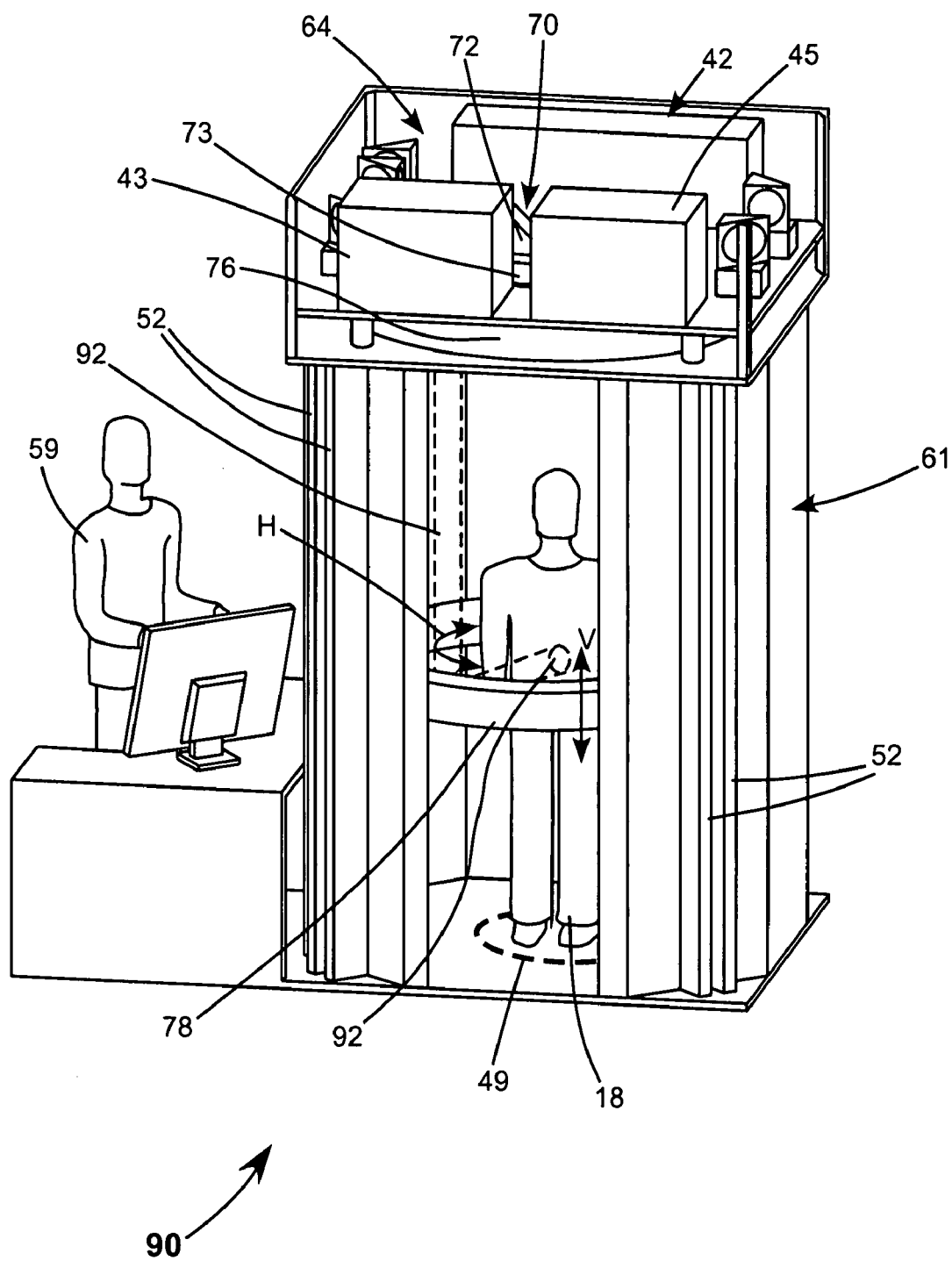
FIG. 6 is three-dimensional view from the rear schematically illustrating yet another embodiment of a terahertz scanning security portal in accordance with the present invention similar to the embodiment of FIG. 3 but wherein a large beam is scanned over the person at different heights to produce a plurality of images each at a different height and scan angle with the images being processed using synthetic aperture radar algorithms to provide a complete image of the person.

FIG. 6 schematically illustrates another embodiment 90 of a THz imaging scanner in accordance with the present invention. Scanner 90 is similar to scanner 60 of FIGS. 3-5 with an exception that optics 64 and ring mirrors 76 and 78 are configured such that a collimated beam 92 of THz radiation is directed from ring mirror 78 onto target person 18. Beam 92 preferably has a maximum dimension of between about 10 and about 500 times greater than a preferred resolution of the scanner, and accordingly simultaneously illuminates a plurality (hundreds) of resolution elements on the person. THz radiation reflected from the target person returns to trans-receiver 42 along the incident path of the radiation. Rotation of rotatable portion 74 of periscope head 70 causes beam 92 to travel around ring mirror 78, with beam 92 correspondingly traveling around the target person as indicated by double arrow H. A series of images taken at various heights V of ring mirror 78 and different beam direction H is processed using synthetic aperture radar algorithms to form an image of all or some portion of the target person having the desired resolution.

An advantage of scanner 90 compared with other above-described embodiments of the present invention is that the use of a large-dimension collimated beam eliminates the need for rapid response, variable-focus optics. Image processing time, however, may be somewhat longer for a processor of comparable processing capacity.

In order to evaluate the potential of the above-described embodiments of the present invention, a number of calculations were performed. Results of these calculations are summarized below.

Regarding "spot" scanners 40 and 60, a desired resolution of 1.0 mm and a scan area (sufficient to cover most persons) of 2.0 meters×0.75 meters (m) is assumed. This results in a number of image cells per image of $1.5 \times 10^6$. A desired scan time is assumed to be five seconds (5.0 s). The scan time per resolution cell (resolution element) is then $3.33 \times 10^{-6}$ seconds. Assuming a five time-constant rule (0.993 for a first-order system), the measurement bandwidth (Effective Measurement Bandwidth) will be $1.5 \times 10^6$. The number of horizontal scan slices, i.e., scans at different heights V, is 2000 and the time for each horizontal scan is 2.5 milliseconds (ms)

The vertical-axis effective scan speed is given by an equation:

$$s_z = L_1/t_1 = 0.4 \text{ m/s} \quad (1)$$

where $L_1$ is the length of the scan area, and $t_1$ is the total scan time for the image.

For the dual-scanning-stage embodiment (scanner 40 of FIG. 2) the effective angular scan rate can be estimated by assuming that scanner head 50 (or ring mirror 78) is located 0.75 m from target person 18. In that case, the rate is given by an equation:

$$d\theta = \arctan(L_2/0.75)t_x = 628 \text{ degrees/s} \quad (2)$$

where $L_2$ is the horizontal width of the scan area and $t_x$ is the time for each horizontal scan.

The choice of operating wavelength, assuming that continuous wave (CW) THz radiation is delivered from the THz trans-receivers 42 or 44, is based on balancing conflicting desires of high-resolution and good penetration of clothing, while taking into account atmospheric data and available wavelengths from THz generators. One preferred wavelength is 192 micrometers (μm), i.e., a frequency of 1.56 THz. This is available from commercially available optically pumped THz lasers. The atmospheric absorption coefficient at 192 μm, in representative indoor conditions, is 0.27 dB/m. Assuming a total, one-way, maximum propagation distance (from trans-receiver via optics 46 to target person 18) of 4.0 m the two-way atmospheric transmission ($T_{atmos}$) loss would be −2.16 dB.

Figure 7:
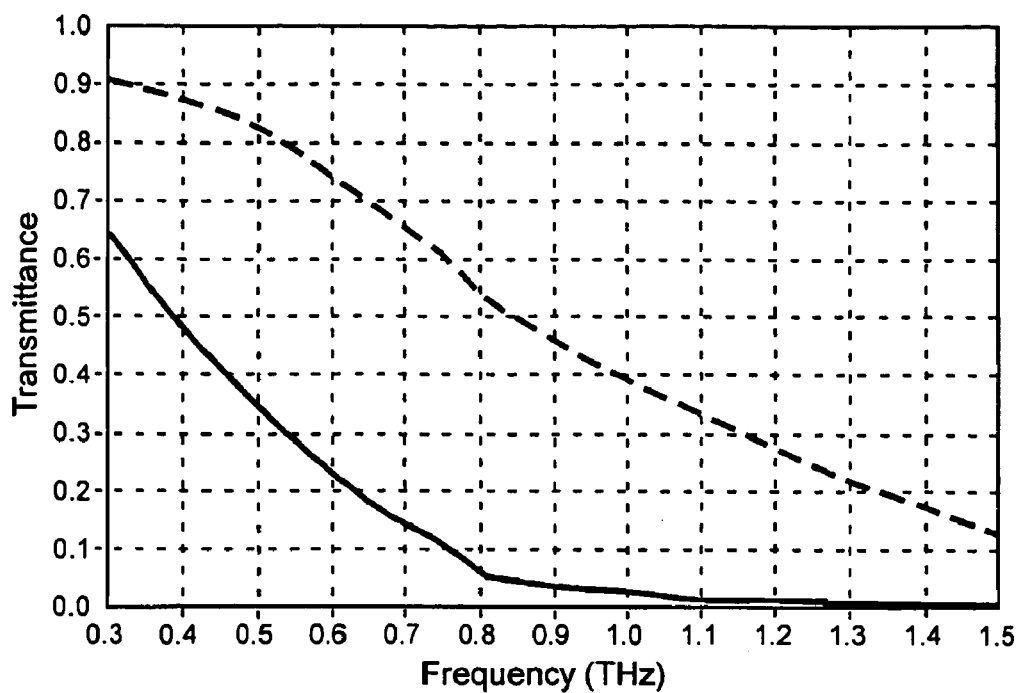
FIG. 7 is a graph reproduced from published data schematically depicting transmission of two types of clothing for THz radiation as a function of THz frequency.

Transmission as a function of frequency for typical clothing materials is presented in graphical form FIG. 7, which is reproduced from published graphs. The dashed and solid curves in FIG. 7 are for a 100% cotton tee-shirt and thick wool coat respectively. Projecting this data slightly to 1.56 THz, and, the one-way clothing transmission ($T_c$) can be estimated to be 0.1. Typical plastics have refractive indexes of about 1.5 at frequencies in the THz range. This leads to a Fresnel reflection ($r_{eff}$) of about 0.04.

Assuming that trans-receivers in the above-described embodiments of the present invention are monostatic symmetric transceivers, i.e., the transmitted (XMIT) and received (RECV) beams are the same size and co-aligned, and assuming a rule-of-thumb that for a Gaussian illumination the resolution is given by an equation:

$$Res = \frac{\pi \cdot \omega_s}{3} \quad (3)$$

where $\omega_s$ is the waist radius of the XMIT beam at the target, then for a desired resolution of 1.0 mm, the waist radius ($\omega_s$) is 0.955 mm. The Rayleigh range of such a beam is 14.9 mm. Because of this, an active variable focus system controlled from rangefinder measurements as described above is required, since the depth variation for typical subjects (target persons) will exceed 30 mm.

In a simple far-field approach where the target person is kept within one Rayleigh range of the geometric focus of the last "lens" in the system, and the depth of the target is 150 mm, it is possible to calculate what the speed of a stage moving such a lens would need to be. In that case the speed would be 48 m/s. This can be reduced by replacing the lens with a multi-lens trans-receiver telescope. The speed will be reduced by the magnification of the telescope.

In order to calculate signal-to-noise ratio (SNR), the geometric scattering (diffuse reflection) loss must first be calculated. In the following example a distance from the trans-receiver aperture to the target of 1.0 m is assumed. The size of this aperture must also be determined. In the case of a coherent system it is not practical to simply take as large an aperture as desired to improve SNR. For a far-field symmetric system of the type considered here, the maximum usable aperture can be calculated by first taking the full-angle divergence ($\theta_{div}$) of the input beam to the far-field projection lens, which in this case is 1.91 milliradians (mrad), and then calculating the effective beam size to produce that divergence from an equation:

$$d_i = \frac{2 \cdot \lambda}{\theta_{div}} \quad (4)$$
$$= 201 \text{ mm}$$

where $\lambda$ is the operating wavelength.

If it is assumed that the target is a diffuse collection of point scatterers (diffuse reflectors), the geometric optical loss factor can then be calculated from an equation:

$$l_o = \frac{\pi \cdot d_i^2}{8 \cdot \pi \cdot R^2} \quad (5)$$
$$= -22.97 \text{ dB}$$

where R is the distance from the target to the collection aperture (1 m in this case).

Regarding safety of scanners in accordance with the present invention, it is assumed that in order to be able to deploy such a scanner commercially it will need to be Safety Class 1. Assuming a transmitter power of 10 mW, and assuming a Gaussian beam, then the peak power density in the scanned beam is given by an equation:

$$P_D = \frac{2 \cdot P_{XMIT}}{\pi \cdot \omega_s^2} \quad (6)$$
$$= 6900 \text{ W/m}^2$$

where $P_{XMIT}$ is the transmitter power.

The exposure time for one resolution cell is 3.3 μs. Accordingly, the peak irradiance on the target person is 23 millijoules per square meter (mJ/m²). The standards for Safety Class 1 only extend as far as 100 μm so that standard is assumed here at 192 μm, lacking any other. That standard is given by an equation:

$$F_{c1} = 5600 \cdot t_e^{0.25} = 239 \text{ J/M}^2 \quad (7)$$

Accordingly, the inventive scanners are Safety Class 1 by a factor of 40 dB.

Using the results discussed above, the SNR for several topologies of trans-receivers that could be used in the inventive scanners can be calculated. In a coherent system, the effect of the measurement bandwidth is given by an equation:

$$BW_{ec} = -10 \text{ LOG}(v_m) = -61.76 \text{ dB} \quad (8)$$

where $v_m$ is the effective measurement bandwidth. This effect is suffered by either a CW coherent trans-receiver or a time domain spectroscopy (TDS) trans-receiver.

In an incoherent trans-receiver, the effect of the measurement bandwidth is given by an equation:

$$BW_{ei} = -10 \text{ LOG } \sqrt{v_m} = -30.88 \text{ dB} \quad (9)$$

assuming a flat power spectral noise density (PSD) function, which is somewhat pessimistic for the Schottky diodes preferred as detectors in trans-receivers used in the present invention, as the 1/f noise in such a detector is dominant for frequencies less than about 1 Gigahertz (GHz).

In an incoherent trans-receiver, wherein the sensitivity for a Schottky diode used as a direct detector is given by an equation:

$$S_i = 10^{-9} W/\sqrt{Hz} \quad (10)$$

The SNR for the scanner looking at plastic under clothing can then be calculated from an equation:

$$SNR = 10 \text{LOG} \left[ \frac{P_{XMIT}}{1000 \cdot S_i} \cdot \frac{1}{\sqrt{v_m}} \cdot T_{atmos} \cdot l_o \cdot T_c^2 \cdot r_{eff} \right] \quad (11)$$

$$= -19.99 \text{ dB}$$

This is lower than would be desirable.

For a coherent trans-receiver such as the trans-receiver of FIG. 1, the Schottky diode sensitivity ($S_c$) is $5 \times 10^{-19}$ (W/Hz) and the SNR is given by an equation:

$$SNR = 10 \text{LOG} \left[ \frac{P_{XMIT}}{1000 \cdot S_c} \cdot \frac{1}{v_m} \cdot T_{atmos} \cdot l_o \cdot T_c^2 \cdot r_{eff} \right] \quad (12)$$

$$= 42.14 \text{ dB}$$

which would be satisfactory in a practical scanner.

The use of a TDS trans-receiver in embodiments of the inventive scanner has been considered. First the available dynamic range (ADR) for such a trans-receiver is calculated. The spectrum for a TDS available from PicoMetrics Inc. of Cambridge, Mass., is graphically depicted in FIG. 8, which is reproduced from manufacturer's data. It is believed that the effective bandwidth of such a trans-receiver is about 1.0 Hz and that other research TDSs would product similar ADR although the spectrum might be shifted somewhat.

Figure 8:
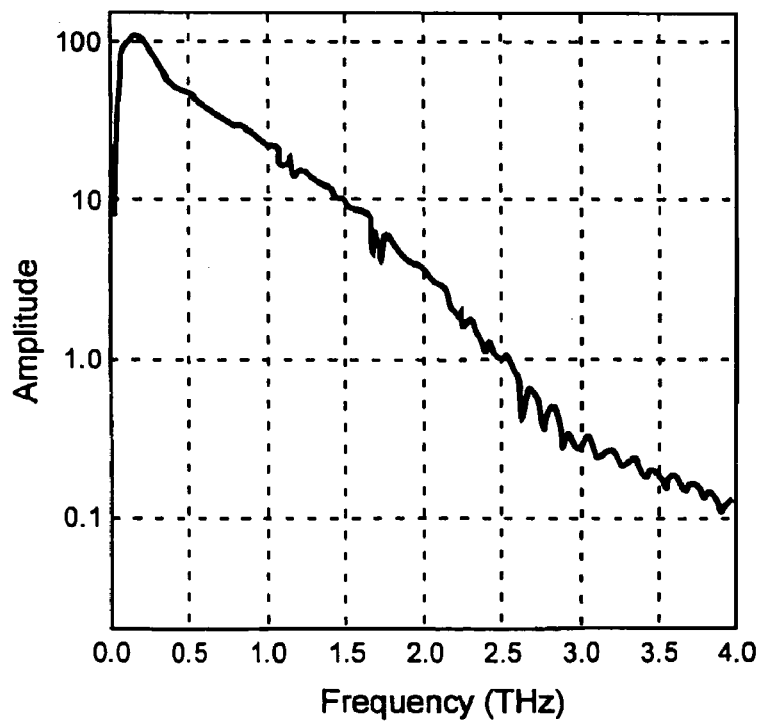
FIG. 8 is a graph reproduced from manufacturer's data schematically illustrating the spectrum of a time domain spectroscopy trans-receiver useable as a trans-receiver in a THz imaging scanner in accordance with the present invention.

In the data of FIG. 8 the ADR at 200 GHz is 60 dB. It is believed that other commercial transceivers are available that will provide this ADR at 1.5 THz With level of ADR, the SNR for a scanner in accordance with the present invention would be given by an equation:

$$SNR = 10 \text{LOG} \left[ 10^{ADR/10} \cdot \frac{1}{v_m} \cdot T_{atmos} \cdot l_o \cdot T_c^2 \cdot r_{eff} \right] \quad (13)$$

$$= -60.87 \text{ dB}$$

This is somewhat less than would be desirable in a practical scanner. Nevertheless the use of TDS trans-receiver is not precluded.

Next, the potential of the SAR (synthetic aperture radar) scanner 90 of FIG. 6 is estimated. Assumptions concerning the scan area ($A_s$), desired resolution (Res), wavelength ($\lambda$) and total area scan time ($t_1$) are the same for as above presented calculations for spot scanners 40 and 60 in accordance with the present invention. Beam 92 is assumed to have an illumination spot waist (ISW) dimension of 35.0 mm. This provides that the number of resolution cells ($N_i$) in each SAR image ($A_s/\pi \cdot \text{ISW}^2$) is 389.767. The angular integration extent ($\Delta \theta = \lambda/2 \cdot \text{Res}$) is 0.096 radians (rad) or 5.496° ($\Delta \theta_d$). The minimum scan time ($t_{sm}$) per illumination area (SAR image) is 0.013, i.e, $t_1/N_i$. The (total) image acquisition time ($t_i$) is about equal to $t_{sm} \cdot N_i$, i.e., equal to about 5 s.

Beam edge target scatterer ranges $y_1$, and $y_2$ at the extents of the illumination scan are determined from the following equations:

$$y_1 = \sqrt{r^2 + \left(\pi \cdot \frac{ISW}{2}\right)^2 - 2 \cdot r \cdot \left(\pi \cdot \frac{ISW}{2}\right) \cdot \cos\left(1.57 + \frac{\Delta\theta}{2}\right)} \quad (14)$$

$$y_1 = \sqrt{r^2 + \left(\pi \cdot \frac{ISW}{2}\right)^2 - 2 \cdot r \cdot \left(\pi \cdot \frac{ISW}{2}\right) \cdot \cos\left(1.57 + \frac{\Delta\theta}{2}\right)} \quad (15)$$

which provide values for $y_1$ and $y_2$ of 505.584 and 500.343 respectively.

Modulo changes from a value $m_1 = 2 \cdot y_1/\lambda$ to a value $m_2 = 2 \cdot y_2/\lambda$ during a scan. This results in a modulo change during the scan ($\Delta m = m_1 - m_2$) of 54.633. Required measurement bandwidth ($v_m$) is about equal to $3 \cdot \Delta m/t_{sm}$, here, $1.278 \times 10^4$ Hz.

In the calculation of SNR a one-way transmission of the THz radiation through air ($T_{00}(\alpha_1)$) from the trans-receiver to the target person is assumed to be 0.78. This is based on an air attenuation coefficient ($\alpha_1$) of 0.27 decibels per meter (dB/m) at a wavenumber of 52.12 cm$^{-1}$, i.e., at a frequency of 1.56 THz or a wavelength of 192 μm. A diffuse reflection loss ($l_0$) of $5 \times 10^{-7}$ is assumed together with a one way loss through clothing ($l_c$) at 1.56 THz of 0.1 and reflectivity of plastics ($r_p$) of 0.04.

The SNR was calculated for a transmitter power of 10.0 mW, i.e., a net equivalent power [NEP] Sc of $5 \times 10^{-19}$ W/Hz from an equation:

$$SNR(r_{eff}, \alpha_1) = 10 \cdot \text{LOG}\left( \frac{P_{XMIT}}{1000 \cdot S_c} \cdot \frac{1}{v_m} \cdot T_{00}(\alpha_1)^2 \cdot l_0 \cdot l_c^2 \cdot r_{eff} \right) \quad (16)$$

where $r_{eff}$ is the effective reflectivity of material to be detected under clothing. Those skilled in the art will recognize that equation (16) is essentially equation (12) with different symbols substituted for certain like variables.

Substituting a value 1.0 for $r_{eff}$ yields a value SNR(1,$\alpha_1$) of 36.776 for detecting metal objects under clothing. Substituting a value 0.04 ($r_p$) for $r_{eff}$ yields a value SNR($r_p,\alpha_1$) of 22.796 for detecting plastic objects under clothing. Even the lowest of these values is believed to be adequate for a practical THz imaging scanner.

Peak irradiance on the target person was calculated to be 0.067 J/m². This is well within the limiting value of $1.885 \times 10^3$ J/m² for a Safety Class 1 device.

It should be noted here that calculations presented above in estimating performance parameters and safety potential of THz imaging scanners in accordance with the present invention are presented merely for guidance and explaining principles of the present invention. These calculations and results thereof should not be considered as limiting the inventive scanners, nor should it be assumed that the calculations are scientifically rigorous.

Further regarding the performance potential of the inventive THz imaging scanners described above, a number of techniques can be employed, in concert with those outlined above, to improve the observed image contrast or reduce image acquisition time. One such technique would involve THz imaging at different THz frequencies or "colors". The specific THz frequencies are chosen to improve differential contrast for specific materials of interest, for example, plastic explosives. In an example wherein only two colors (THz frequencies) are employed, one is chosen to coincide with a spectral feature in the plastic explosive and the other to specifically not coincide with such a feature. The difference between signals at these two THz frequencies from corresponding area is displayed as the image of the target person. Using this multispectral technique, image contrast can be expected to be significantly higher than in an image from signals recorded at only one of the THz frequencies. If a number of materials, each having different spectral features, are of interest, then more than two THz frequencies can be employed. This technique provides not only for improving contrast but also for providing material identification in an image via color coding or the like.

Another enhancement technique that can be applied in the above described THz imaging scanners is phase contrast imaging. As the inventive scanners are fully-coherent, the scanners provide not only amplitude data, but also provide phase data in the manner of a vector network analyzer. Images can be displayed using either the amplitude data or phase data. In the case of plastic explosive it is believed that a phase contrast image would provide good definition of the edge of the explosive. An amplitude image can then be concentrated on the area in and around the defined edge to provide more accurate identification of the material within the defined edge.

Yet another enhancement technique involves "fusing" data from the THz trans-receiver with data from a sensor at a substantially different operating frequency. Examples might include a mm-wave sensor or an IR camera. In this embodiment, the sensor data fusion can be utilized to either enhance contrast, or "cue" an operator of the inventive scanner to "take a harder look" at a specific area. By way of example, if a mm-wave sensor proved to be good at quickly distinguishing and area of interest on a target person but did not offer sufficient resolution for positive identification of a suspect object or substance, the mm-wave data could be used to "cue" the THz trans-receiver to examine only the area of interest. In this way the additional sensor could not only improve contrast, but could improve acquisition time by enabling the THz system to only perform high resolution scans of areas in an area of interest which would usually be a relatively small fraction of a the projected area of a person.

Other embodiments of the inventive THz imaging scanners will be evident from the drawings and the above-presented detailed description of preferred embodiments of the present invention. The application, however, is not limited to the above-described embodiments. Rather the application is limited only by the claims appended hereto.

What is claimed is:

1. Apparatus for examining a clothed person for detecting an object or substance concealed by the person's clothing, the apparatus comprising:

a portal defining a position in the apparatus in which the person is positioned for examination;

a terahertz (THz) trans-receiver arranged to provide a beam of THz radiation having a frequency such that the THz radiation is transmitted by the positioned person's clothing;

an optical system for directing a beam of THz radiation from the THz trans-receiver to the positioned person and directing radiation reflected from the positioned person back to the THz trans-receiver, the optical system including a vertically movable mirror for directing the beam to a plurality of different heights on the positioned person and an angular scanning device for moving the beam to a plurality of different horizontal locations on the positioned person along each of the plurality of different heights; and signal processing electronics for recording data including at least one parameter of radiation reflected from the positioned person at the different heights and locations therealong and for processing the recorded data to provide an image of at least some portion of the positioned person.

2. The apparatus of claim 1, wherein the movable mirror and the scanning device of the optical system are incorporated in a scanner head vertically movable in vertically oriented guides attached to the portal.

3. The apparatus of claim 1, wherein the vertically movable mirror is a ring mirror vertically movable in vertically oriented guides attached to the portal and having a diameter sufficient to encircle the person, wherein there optical system further includes a ring mirror fixedly attached to the portal at a height thereon above the positioned person and the scanning device is a periscope head including a rotatable mirror; and wherein the rotatable mirror directs the THz-radiation beam horizontally to the fixed ring mirror, the fixed ring mirror, directs the THz-radiation beam vertically to the movable ring mirror, and the movable ring mirror directs the THz-radiation beam laterally to the person.

4. The apparatus of claim 1, wherein the apparatus has a predetermined target resolution dimension and the optical system is arranged to focus the THz-radiation beam on the person with the a maximum dimension of the focused THz-radiation beam being about equal to the target resolution dimension.

5. The apparatus of claim 4, wherein the maximum beam dimension on the person is about one millimeter or less.

6. The apparatus of claim 4, wherein the optical system includes a rangefinder arranged to measure an instant distance of the person from the THz trans-receiver, and wherein the optical system is an active variable-focus system arranged to focus the beam on the person in response to the rangefinder measurement.

7. The apparatus of claim 1, wherein the apparatus has a predetermined target resolution dimension defining a target resolution element, wherein the optical system is arranged to deliver the THz-radiation beam on the person with a maximum dimension of the THz-radiation beam being sufficient that the beam illuminates a plurality of target resolution elements, and wherein the recorded parameters are processed using synthetic aperture radar algorithms to provide the image of at least some portion of the positioned person.

8. The apparatus of claim 7, wherein the target resolution dimension is about 1.0 millimeter or less and the THz-radiation beam on the person has a maximum dimension of about 35 millimeters.

9. The apparatus of claim 1, wherein the parameters of radiation reflected from the positioned person is the phase of the radiation and the image provided is a phase-contrast image.

10. The apparatus of claim 1, wherein the THz radiation has a frequency of about 1.56 THz.

11. Apparatus for examining a clothed person for detecting an object or substance concealed by the person's clothing, the apparatus comprising:
- a portal defining a position in the apparatus in which the person is positioned for examination;
- first and second terahertz (THz) trans-receivers for delivering first and second beams of terahertz radiation having respectively first and second wavelengths at which the positioned person's clothing is at least partially transparent;
- an optical system arranged to direct the beams of THz radiation from the THz trans-receivers to a plurality of areas on the positioned person at different heights on the positioned person and at a plurality of different horizontal locations on the positioned person along each of the plurality of different heights, the optical system being further arranged to direct THz radiation reflected from the positioned person back to the THz trans-receivers; and
- signal processing electronics for recording data including at least one parameter of radiation reflected from the positioned person at the different heights and locations therealong at each of the different wavelengths and for processing the recorded data to provide an image of at least some portion of the positioned person.

12. The apparatus of claim 11, wherein the optical system includes first and second vertically movable mirrors for directing respectively the first and second beams of terahertz radiation to the plurality of different heights on the positioned person and first and second angular scanning devices for moving the beams to the plurality of different horizontal locations on the person along each of the plurality of different heights.

13. Apparatus for examining a clothed person for detecting an object or substance concealed by the person's clothing, the apparatus comprising:
- a portal defining a position in the apparatus in which the person is positioned for examination;
- a terahertz (THz) trans-receiver arranged to provide a beam of THz radiation having a frequency such that the THz radiation is at least partially transmitted by the person's clothing;
- an optical system for directing a beam of THz radiation from the THz trans-receiver to the positioned person and directing radiation reflected from the position person back to the THz trans-receiver, the optical system including a rotatable mirror encircled by a fixed ring mirror located at a height above the person and a vertically movable ring mirror located below the fixed ring mirror and having a diameter sufficient that the mirror can encircle the positioned person, the beam being directed from the rotatable mirror to the fixed ring mirror from the fixed ring mirror to the movable ring mirror and from the movable ring mirror to the positioned person and wherein vertically moving the movable ring mirror directs the beam to a plurality of different heights on the positioned person and rotating the rotatable mirror moves the beam to a plurality of different horizontal locations on the person along each of the plurality of different heights; and
- signal processing electronics for recording data including at least one parameter of radiation reflected from the positioned person at the different heights and locations therealong and for processing the recorded data to provide an image of at least some portion of the positioned person.

14. The apparatus of claim 13, wherein the apparatus has a predetermined target resolution dimension and the optical system is arranged to focus the THz-radiation beam on the person with the a maximum dimension of the focused THz-radiation beam being about equal to the target resolution dimension.

15. The apparatus of claim 14, wherein the maximum beam dimension on the person is about one millimeter or less.

16. The apparatus of claim 14, wherein the optical system includes a rangefinder arranged to measure an instant distance of the person from the THz trans-receiver, and wherein the optical system is an active variable-focus system arranged to focus the beam on the person in response to the rangefinder measurement.

17. The apparatus of claim 13, wherein the apparatus has a predetermined target resolution dimension defining a target resolution element, wherein the optical system is arranged to deliver the THz-radiation beam on the person with a maximum dimension of the THz-radiation beam being sufficient that the beam illuminates a plurality of target resolution elements, and wherein the recorded parameters are processed using synthetic aperture radar algorithms to provide the image of at least some portion of the positioned person.

18. The apparatus of claim 17, wherein the target resolution dimension is about 1.0 millimeter or less and the THz-radiation beam on the person has a maximum dimension of about 35 millimeters.

19. The apparatus of claim 13, wherein the parameters of radiation reflected from the positioned person is the phase of the radiation and the image provided is a phase-contrast image.

* * * * *